United States Patent
Nakamura et al.

(10) Patent No.: US 11,434,322 B2
(45) Date of Patent: Sep. 6, 2022

(54) SULFOBETAINE GROUP-COMPRISING REACTIVE COMPOUND, POLYMER THEREOF, AND METHOD OF PRODUCING THE POLYMER

(71) Applicant: Nagase ChemteX Corporation, Osaka (JP)

(72) Inventors: Daisuke Nakamura, Hyogo (JP); Tatsuya Inoue, Hyogo (JP)

(73) Assignee: NAGASE CHEMTEX CORPORATION, Osaka (JP)

( * ) Notice: Subject to any disclaimer, the term of this patent is extended or adjusted under 35 U.S.C. 154(b) by 492 days.

(21) Appl. No.: 16/493,426

(22) PCT Filed: Mar. 21, 2018

(86) PCT No.: PCT/JP2018/011230
§ 371 (c)(1),
(2) Date: Sep. 12, 2019

(87) PCT Pub. No.: WO2018/174111
PCT Pub. Date: Sep. 27, 2018

(65) Prior Publication Data
US 2020/0131300 A1    Apr. 30, 2020

(30) Foreign Application Priority Data

Mar. 24, 2017 (JP) .............................. JP2017-059084

(51) Int. Cl.
| | | |
|---|---|---|
| *C07C 309/14* | (2006.01) | |
| *C08G 18/38* | (2006.01) | |
| *A61L 31/06* | (2006.01) | |
| *C08G 18/44* | (2006.01) | |
| *C08G 18/65* | (2006.01) | |
| *C08G 18/76* | (2006.01) | |
| *C08J 5/18* | (2006.01) | |

(52) U.S. Cl.
CPC .......... *C08G 18/3857* (2013.01); *A61L 31/06* (2013.01); *C07C 309/14* (2013.01); *C08G 18/44* (2013.01); *C08G 18/6529* (2013.01); *C08G 18/7671* (2013.01); *C08J 5/18* (2013.01); *C08J 2375/04* (2013.01)

(58) Field of Classification Search
CPC . C08G 18/3857; C07C 309/14; C08J 2375/04
See application file for complete search history.

(56) References Cited

U.S. PATENT DOCUMENTS

| | | | |
|---|---|---|---|
| 2006/0041160 A1 | 2/2006 | Nagase et al. | |
| 2010/0036081 A1* | 2/2010 | Nagase | C07F 9/091 |
| | | | 528/72 |

FOREIGN PATENT DOCUMENTS

| | | |
|---|---|---|
| CN | 101429287 | 5/2009 |
| JP | 2015-61901 | 4/2015 |
| WO | 2004/074298 | 9/2004 |
| WO | 2008/029744 | 3/2008 |
| WO | 2016/132993 | 8/2016 |

OTHER PUBLICATIONS

Extended European Search Report dated Feb. 18, 2020 in corresponding European Patent Application No. 18772000.8.
International Search Report, dated Apr. 17, 2018 in corresponding International Patent Application No. PCT/JP2018/011230.

* cited by examiner

*Primary Examiner* — Kuo Liang Peng
(74) *Attorney, Agent, or Firm* — Wenderoth, Lind & Ponack, L.L.P.

(57) ABSTRACT

A polymer comprising at least 1% by mole of a structural unit represented by Formula (2);

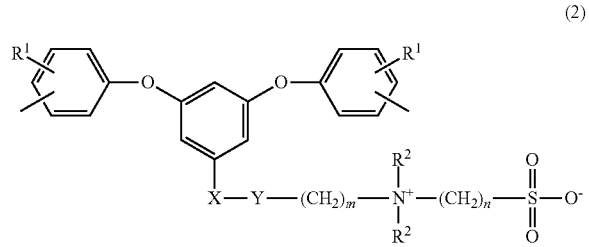

(2)

in Formula (2), two $R^1$s are the same or different from each other and are each a hydrogen atom or an alkyl group having 1 to 6 carbon atoms; X is a single bond, an oxygen atom, or a group represented by —COO—, —OOC—, —CONH—, —NH—, —NHCO—, —$NR^3$—, or —$CH_2O$—; Y is a single bond or an oligooxyalkylene group; two $R^2$s are the same or different from each other and are each an alkyl group having 1 to 6 carbon atoms; $R^3$ is an alkyl group having 1 to 6 carbon atoms; m is an integer of 1 to 10; and n is an integer of 2 to 10; and having a number average molecular weight of 5,000 or more has various characteristics suitable for use in contact with a living organism and can be easily produced.

13 Claims, 1 Drawing Sheet

PET FILM: D
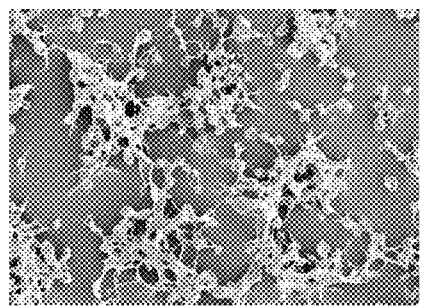
COMPARATIVE EXAMPLE 1(SPUU):C
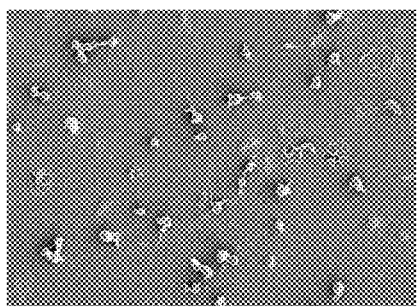
EXAMPLE 4 (SPUUSBB30):A
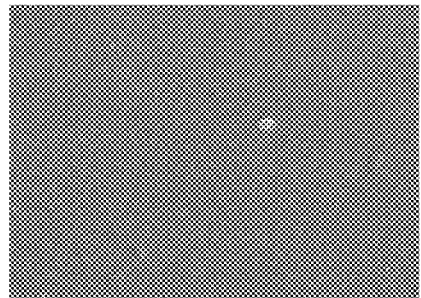
EXAMPLE 6 (SPUUSBB6):B
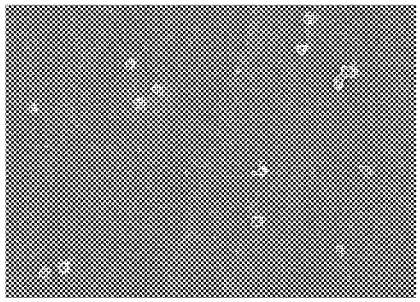

SULFOBETAINE GROUP-COMPRISING REACTIVE COMPOUND, POLYMER THEREOF, AND METHOD OF PRODUCING THE POLYMER

TECHNICAL FIELD

The present invention relates to a biocompatible polymer mainly used in the medical field, a method for producing the polymer, and a monomer compound constituting the polymer.

BACKGROUND ART

When an artificial organ, an artificial tissue, a medical device, or the like is implanted in or is used in contact with a living organism, the living organism may cause defense reaction against such an artificial substance. When an artificial material comes into contact with a living organism, first, plasma proteins adsorb thereto, and through the adsorbing proteins, cells adhere to the surface of the artificial material. As a result, blood clots may be formed in blood to attach to the artificial material surface, or the artificial material is covered with a collagen fiber capsule in connective tissue. Accordingly, the artificial material cannot exert its intended function as an alternative to a living material. When coming into contact with a living organism, an artificial material may activate complements in plasma, and this causes a series of immune reactions to kill self cells.

To solve such problems, biocompatible materials having no or small interaction with biogenic substances such as proteins and blood cells have been developed. In the biomedical field, polyethylene glycol (PEG) and materials with PEG have been generally used due to their characteristics including high biocompatibility and hydrophilicity. PEG, however, loses its repulsive characteristics to proteins at 35° C. or more and is likely to adhere to proteins unfortunately.

Biomembrane lipids have a phosphorylcholine (PC) group as a phospholipid polar group, and thus a polymer of 2-methacryloyloxyethyl phosphorylcholine (MPC) having a PC group has been developed (Non-Patent Literature 1). The MPC polymer has a methacryloyl group having excellent polymerizability, and thus copolymerization with various vinyl monomers enables free molecular design for intended purposes. For example, a homopolymer of MPC is water-soluble and thus is unsuited as a medical material used in living organisms, but selection of a vinyl monomer to be copolymerized can yield a water-insoluble copolymer.

Such a water-insoluble MPC copolymer, however, still has a problem that alcohols commonly used in medical practice may eliminate or dissolve the polymer. In addition, due to a flexible main chain structure, the copolymer has no heat resistance against autoclave sterilization and has insufficient hydrolysis resistance and mechanical strength.

A polymer prepared by polymerization of a monomer having a PC group and a polyurethane prepolymer has also been developed (Patent Literatures 1, 2). The monomer having a PC group, however, has high hygroscopic properties and thus is difficult to synthesize or handle except in a nonaqueous environment.

There is accordingly a demand for a biocompatible material that has various characteristics for use in contact with a living organism and can be easily produced.

CITATION LIST

Patent Literature

Patent Literature 1: International Publication WO 2008/029744 (Japanese Patent No. 5276443)

Patent Literature 2: International Publication WO 2004/074298 (Japanese Patent No. 4628951)

Non Patent Literature

Non-Patent Literature 1: Polymer Journal, vol. 22, page 355, 1990

SUMMARY OF INVENTION

Technical Problem

The object of the present invention is to provide a biocompatible material that has various characteristics suitable for use in contact with a living organism and can be easily produced.

Solution to Problem

The inventors of the present invention have carried out intensive studies in order to solve the above problems and have found that a polymer comprising at least 1% by mole of a structural unit represented by Formula (2):

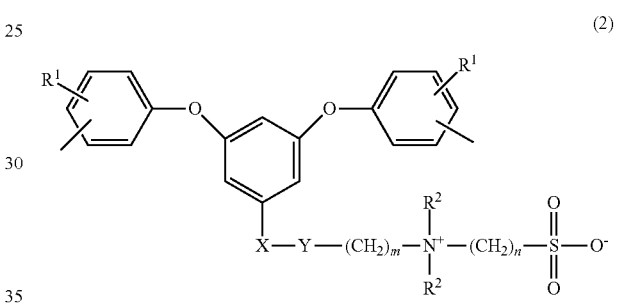

(2)

(in Formula (2), two $R^3$s are the same or different from each other and are each a hydrogen atom or an alkyl group having 1 to 6 carbon atoms; X is a single bond, an oxygen atom, or a group represented by —COO—, —OOC—, —CONH—, —NH—, —NHCO—, —$NR^3$—, or —$CH_2O$—; Y is a single bond or an oligooxyalkylene group; two $R^2$s are the same or different from each other and are each an alkyl group having 1 to 6 carbon atoms; $R^3$ is an alkyl group having 1 to 6 carbon atoms; m is an integer of 1 to 10; and n is an integer of 2 to 10)
and having a number average molecular weight of 5,000 or more has high biocompatibility and also has practically sufficient heat resistance and mechanical strength.

The present invention has been completed on the basis of the above findings and provides the following aspects [1] to [13].

[1] A compound represented by Formula (1):

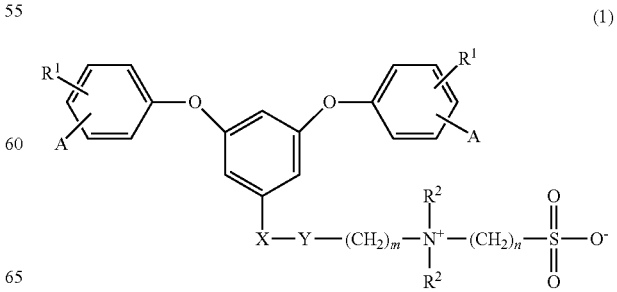

(1)

(in Formula (1), two $R^1$s are the same or different from each other and are each a hydrogen atom or an alkyl group having 1 to 6 carbon atoms; As("A"s) are the same or different from each other and are each a substituent comprising an amino group, a hydroxy group, an epoxy group, or a (meth)acryloyl group; X is a single bond, an oxygen atom, or a group represented by —COO—, —OOC—, —CONH—, —NH—, —NHCO—, —$NR^3$—, or —$CH_2O$—; Y is a single bond or an oligooxyalkylene group; two $R^2$s are the same or different from each other and are each an alkyl group having 1 to 6 carbon atoms; $R^3$ is an alkyl group having 1 to 6 carbon atoms; m is an integer of 1 to 10; and n is an integer of 2 to 10).

[2] The compound according to [1], wherein each A is a substituent comprising an amino group.

[3] The compound according to [1] or [2], wherein n is an integer of 3 to 5.

[4] A polymer comprising at least 1% by mole of a structural unit represented by Formula (2):

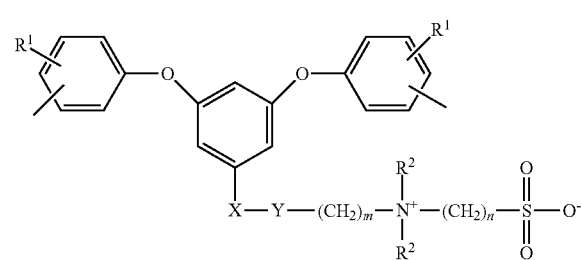

(2)

(in Formula (2), two $R^1$s are the same or different from each other and are each a hydrogen atom or an alkyl group having 1 to 6 carbon atoms; X is a single bond, an oxygen atom, or a group represented by —COO—, —OOC—, —CONH—, —NH—, —NHCO—, —$NR^3$—, or —$CH_2O$—; Y is a single bond or an oligooxyalkylene group; two $R^2$s are the same or different from each other and are each an alkyl group having 1 to 6 carbon atoms; $R^3$ is an alkyl group having 1 to 6 carbon atoms; m is an integer of 1 to 10; and n is an integer of 2 to 10) and having a number average molecular weight of 5,000 or more.

[5] The polymer according to [4], wherein the polymer has a bond selected from the group consisting of an amide bond, a urethane bond, a urea bond, and an imide bond in a main chain skeleton thereof.

[6] The polymer according to [4], comprising at least 1% by mole of the structural unit represented by Formula (2) and a structural unit comprising an isocyanate group-terminated urethane prepolymer prepared by reacting a diisocyanate compound and a diol compound, and having a number average molecular weight of 5,000 or more.

[7] The polymer according to [6], wherein the polymer has a urethane bond and a urea bond in a main chain skeleton thereof.

[8] The polymer according to any one of [4] to [7], wherein n is an integer of 3 to 5.

[9] A film, sheet, fiber, or membrane comprising the polymer according to any one of [4] to [8].

[10] A medical product comprising the polymer according to any one of [4] to [8].

[11] A method for producing the polymer according to [4], the method comprising a step of subjecting the compound represented by Formula (1) and an additional polymerizable monomer to polycondensation reaction, polyaddition reaction, or radical polymerization reaction or a step of reacting a polymerizable monomer comprising the compound represented by Formula (1) with a functional group-terminated prepolymer capable of reacting therewith.

[12] The production method according to [11], wherein the produced polymer has a bond selected from the group consisting of an amide bond, a urethane bond, a urea bond, and an imide bond in a main chain skeleton thereof.

[13] The production method according to [11], wherein the substituent A in Formula (1) comprises an amino group or a hydroxy group, and the functional group-terminated prepolymer capable of reacting with the compound represented by Formula (1) is an isocyanate group-terminated urethane prepolymer prepared by reacting a diisocyanate compound and a diol compound.

Advantageous Effects of Invention

Polymers having a sulfobetaine group have been considered to have a lower biocompatibility than polymers having a phosphorylcholine group. However, the polymer having a sulfobetaine group of the present invention has sufficient biocompatibility and also has excellent heat resistance and mechanical strength.

A medical material to be implanted in a living organism or to be used in contact with a living organism is required to withstand autoclave sterilization (120° C., 1 atmosphere) as a general sterilization method. The polymer of the present invention withstands the autoclave sterilization.

A medical material to be implanted in a living organism or to be used in contact with a living organism is required to have an appropriate elasticity in many cases in order not to apply mechanical stress to the living organism. The medical material is also required to have such a strength as not to be broken under stretching. In particular, a material used as a covering material is required to have a high rupture strength and a high breaking elongation. The polymer of the present invention has both a sufficient rupture strength and a sufficient breaking elongation and thus can be widely used.

A typical monomer having high hygroscopic properties is difficult to feed for polymerization reaction or is likely to be fed in an unintended amount except in a nonaqueous environment, unfortunately. In contrast, the monomer compound of the present invention to be used to produce the polymer of the present invention has lower hygroscopic properties than monomers having a phosphorylcholine group and thus is easily handled. In addition, the monomer compound of the present invention can be synthesized through a shorter process than monomers having a phosphorylcholine group. The monomer compound of the present invention can be synthesized without the need of a reaction in a closed system under heating, which is needed in synthesis of monomers having a phosphorylcholine group, and thus can be produced inexpensively. Hence, the polymer of the present invention can also be synthesized simply and inexpensively as compared with polymers having a phosphorylcholine group.

BRIEF DESCRIPTION OF DRAWINGS

FIG. 1 are scanning electron micrographs showing platelet adsorption degrees to test pieces of a PET film, Comparative Example 1, Example 4, and Example 6.

DESCRIPTION OF EMBODIMENTS

The present invention will now be described in detail.
(1) Reactive Compound Having Sulfobetaine Group Compound of Present Invention A compound of the present invention is a reactive compound having a sulfobetaine group represented by Formula (1):

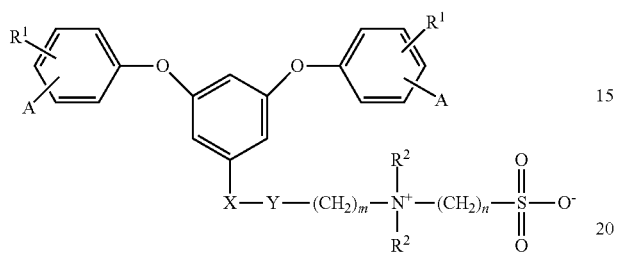

(1)

(in Formula (1), two $R^1$s are the same or different from each other and are each a hydrogen atom or an alkyl group having 1 to 6 carbon atoms; As are the same or different from each other and are each a substituent comprising an amino group, a hydroxy group, an epoxy group, or a (meth)acryloyl group; X is a single bond, an oxygen atom, or a group represented by —COO—, —OOC—, —CONH—, —NH—, —NHCO—, —$NR^3$—, or —$CH_2O$—; Y is a single bond or an oligooxyalkylene group; two $R^2$s are the same or different from each other and are each an alkyl group having 1 to 6 carbon atoms; $R^3$ is an alkyl group having 1 to 6 carbon atoms; m is an integer of 1 to 10; and n is an integer of 2 to 10).

Examples of the alkyl group having 1 to 6 carbon atoms as $R^1$ include a methyl group, an ethyl group, a propyl group, an isopropyl group, a butyl group, a sec-butyl group, a tert-butyl group, a pentyl group, and a hexyl group. Two $R^1$s are preferably the same and a hydrogen atom.

The reactive group contained in the substituent A is preferably a hydroxy group or an amino group. A hydroxy group can form a urethane bond together with an isocyanate group, whereas an amino group can form a urea bond together with an isocyanate group, and thus these groups enable production of a polymer having high mechanical strength. When the reactive group contained in the substituent A is an amino group, a polymer having particularly high mechanical strength can be produced.

The functional groups contained in the two substituents A are preferably the same. Specifically, each of the two substituents A preferably has an amino group, a hydroxy group, an epoxy group, or a (meth)acryloyl group. The two substituents A are more preferably the same.

X is preferably —COO— or —CONH— and is more preferably —COO—. When X is —COO—, the compound of Formula (1) can be simply synthesized, and a highly biodegradable polymer can be produced. When X is —CONH—, the compound of Formula (1) and a resulting polymer have higher resistance to acid and alkali.

When X is —$NR^3$—, examples of the alkyl group having 1 to 6 carbon atoms as $R^3$ include a methyl group, an ethyl group, a propyl group, an isopropyl group, a butyl group, a sec-butyl group, a tert-butyl group, a pentyl group, and a hexyl group. $R^3$ is preferably an alkyl group having 1 to 3 carbon atoms in terms of small steric hindrance and is more preferably a methyl group.

The oligooxyalkylene group as Y means an oxyalkylene group having 2 to 12 carbon atoms and 1 to 3 oxygen atoms, specifically, —$(CH_2CH_2O)_q$—, —$(CH_2CH_2CH_2O)_q$—, or —$(CH_2CH_2CH_2CH_2O)_q$— (each q is an integer of 1 to 3). Y is preferably a single bond. Two $R^2$s are preferably the same and an alkyl group having 1 to 3 carbon atoms and are more preferably a methyl group.

m is preferably an integer of 2 to 6 and is more preferably 2. n is preferably an integer of 2 to 6, more preferably an integer of 3 to 5, and most preferably 4.

Method for Producing Compound of Present Invention

The compound of Formula (1) can be produced, for example, by the method described below.

(a) When a is a Substituent Comprising an Amino Group

When A is a substituent comprising an amino group, an example in which A is an amino group will be described. For example, first, a dinitro compound represented by Formula (3):

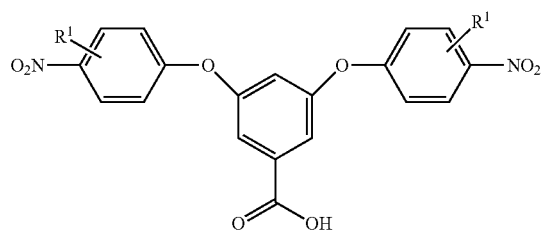

(3)

is reacted with a compound represented by Formula (4):

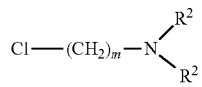

(4)

to synthesize a compound represented by Formula (5).

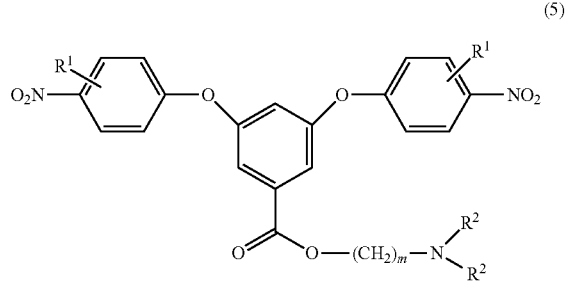

(5)

Next, the compound represented by Formula (5) is reacted with a sultone compound represented by Formula (6):

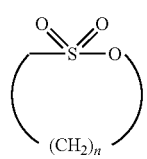

(6)

to synthesize a compound having a sulfobetaine group represented by Formula (7)

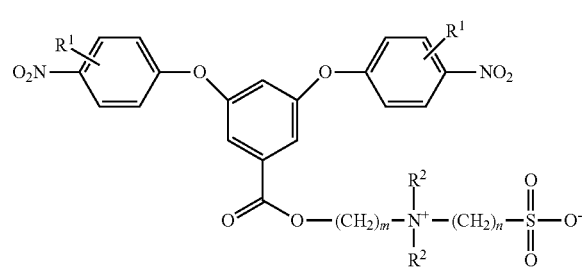

(7)

Finally, two nitro groups of the compound represented by Formula (7) are reduced into amino groups, giving a compound represented by Formula (8).

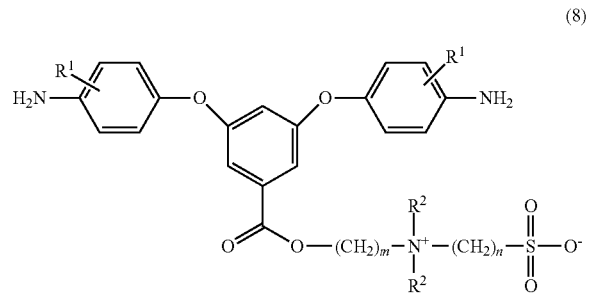

(8)

In Formulae (3) to (8), $R^1$, $R^2$, m, and n are as defined in Formula (1).

The compound represented by Formula (3) can be synthesized in accordance with a method in the examples described later, from a commercially available compound through a known reaction.

The above synthetic method is a method of synthesizing a compound represented by Formula (1) in which X is —COO—, and Y is a single bond. In the synthetic method, HCl elimination reaction is performed between —COOH of the compound of Formula (3) and —Cl of the compound of Formula (4). When X or Y in Formula (1) is another group, for example, the compound of Formula (3) can be so changed as to have a substituent that can undergo HCl elimination reaction with —Cl of the compound of Formula (4).

For the reaction of the compound of Formula (3) and the compound of Formula (4), the compounds are preferably used at a molar ratio (compound of Formula (3):compound of Formula (4)) of 1:1 to 1:5, and are preferably reacted in the presence of a tertiary amine such as triethylamine to trap hydrogen chloride generated, or are preferably reacted while an inert gas is blown into the reaction system and remove hydrogen chloride out of the system.

In the ring-opening addition reaction of the compound of Formula (5) and the sultone compound of Formula (6), the compounds are preferably used at a molar ratio (compound of Formula (5):sultone compound) of 1:1 to 1:10.

In place of the reaction of the compound of Formula (5) and the sultone compound of Formula (6), the compound of Formula (5) can be reacted with a 1,3-dihalogenated alkane (having 2 to 10 carbon atoms) to give a quaternary ammonium salt, then the salt can be reacted with a sulfite, and consequently, the compound of Formula (7) can be prepared. The reaction is specifically disclosed, for example, in JP 1998-87601 A.

The reduction of the nitro groups of the compound of Formula (7) can be performed by catalytic reduction in a hydrogen gas atmosphere with a metal catalyst such as nickel, platinum, palladium, and rhodium. Alternatively, the reduction can be performed by reacting the compound of Formula (7) with a reducing agent such as diborane, lithium borohydride, sodium borohydride, sodium aluminum hydride, sodium dialkoxyaluminum hydride, and sodium diethylaluminum hydride. In this case, the reaction is accelerated in the presence of a catalyst such as tin chloride.

Each reaction to synthesize the compound of Formula (8) from the compound of Formula (3) is preferably performed in a solvent. The solvent may be any solvent that does not interfere with the reaction, and examples include alcohols such as methanol, ethanol, and isopropyl alcohol; glycols such as ethylene glycol and propylene glycol; ketones such as acetone and methyl ethyl ketone; alkyl ethers such as diethyl ether, tetrahydrofuran, and dimethoxyethane; aromatic compounds such as benzene, toluene, and xylene; aliphatic hydrocarbon compounds such as n-hexane; alicyclic hydrocarbon compounds such as cyclohexane; acetates such as methyl acetate and ethyl acetate; dimethylacetamide; dimethylsulfoxide; dioxane; N-methylpyrrolidone; dimethylformamide; and chloroform.

The reaction temperature is preferably about −100 to 150° C., more preferably about −50 to 100° C., and even more preferably about 0 to 50° C.

(b) When a is a Substituent Comprising a Hydroxy Group

When A is a substituent comprising a hydroxy group, an example in which A is a hydroxy group will be described. For example, first, a compound represented by Formula (9):

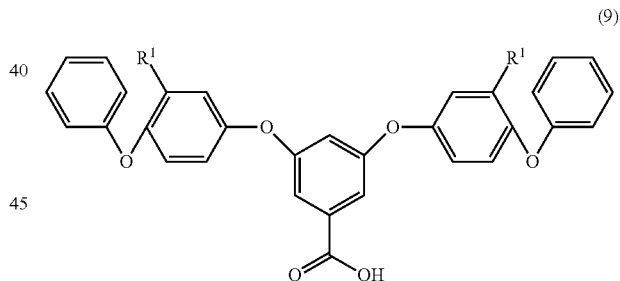

(9)

is reacted with the compound of Formula (4) to synthesize a compound represented by Formula (10).

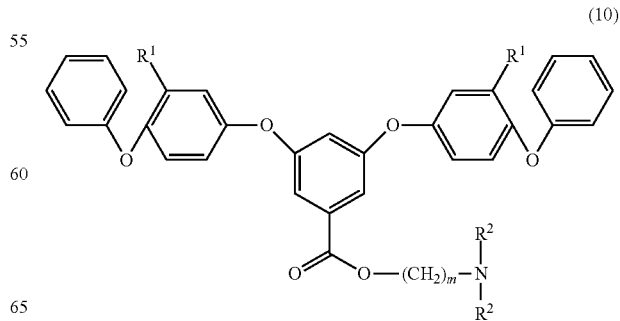

(10)

Next, the compound represented by Formula (10) is reacted with the sultone compound represented by Formula (6) to synthesize a compound having a sulfobetaine group represented by Formula (11).

(11)

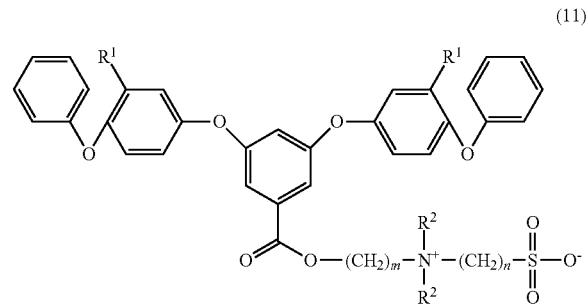

Finally, two phenoxy moieties of the compound represented by Formula (11) are reduced into hydroxy groups, giving a compound represented by Formula (12).

(12)

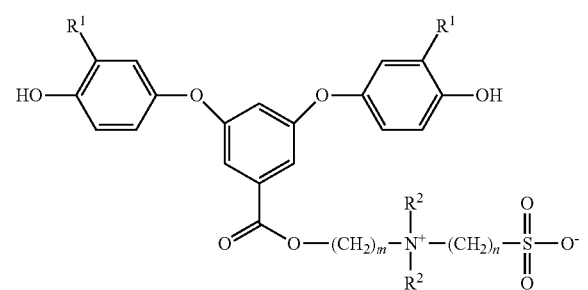

In Formulae (9) to (12), $R^1$, $R^2$, m, and n are as defined in Formula (1).

For all the reactions from the compound of Formula (9) to the compound represented by Formula (12), the synthesis conditions from the compound represented by Formula (3) to the compound represented by Formula (8) can be applied.

(c) When a is a Substituent Comprising an Epoxy Group

When A is a substituent comprising an epoxy group, an example in which A is an epoxy group will be described. For example, the compound represented by Formula (12) is reacted with epichlorohydrin to give a compound represented by Formula (13).

(13)

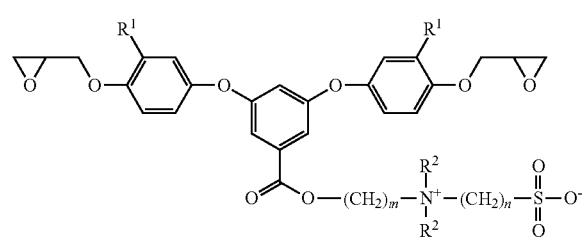

Alternatively, for example, the compound represented by Formula (8) is reacted with epichlorohydrin to give a compound represented by Formula (14).

(14)

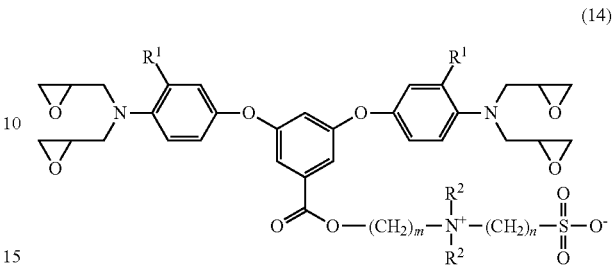

In Formula (13) and Formula (14), $R^1$, $R^2$, m, and n are as defined in Formula (1).

(d) When a is a Substituent Comprising a (Meth)Acryloyl Group

When A is a substituent comprising a (meth)acryloyl group, an example in which A is a (meth)acryloyl group will be described. For example, the compound represented by Formula (12) is reacted with (meth)acryloyl chloride to give a compound represented by Formula (15).

(15)

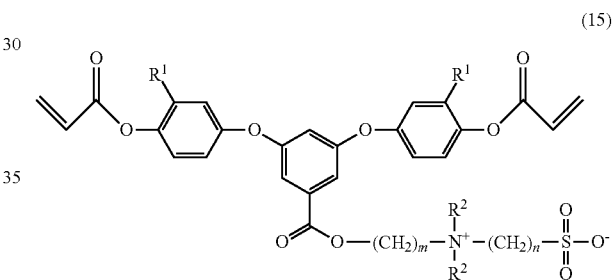

In Formula (15), $R^1$, $R^2$, m, and n are as defined in Formula (1)

(2) Polymer Having Sulfobetaine Group

Polymer of Present Invention

The polymer of the present invention comprises at least 1% by mole of a structural unit represented by Formula (2):

(2)

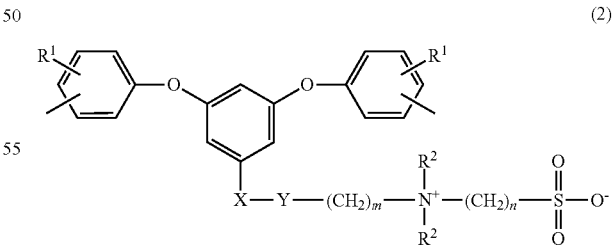

(in Formula (2), two R's are the same or different from each other and are each a hydrogen atom or an alkyl group having 1 to 6 carbon atoms; X is a single bond, an oxygen atom, or a group represented by —COO—, —OOC—, —CONH—, —NH—, —NHCO—, —NR³—, or —CH₂O—; Y is a single bond or an oligooxyalkylene group; two R²s are the same or different from each other and are each an alkyl group having 1 to 6 carbon atoms; $R^3$ is an alkyl group having 1 to 6 carbon atoms; m is an integer of 1 to 10; and n is an integer of 2 to 10)
and has a number average molecular weight of 5,000 or more.

Preferred examples of $R^1$, $R^2$, $R^3$, X, Y, m, and n are as described for the compound of Formula (1).

The polymer of the present invention typically has a number average molecular weight of 5,000 or more and may have a number average molecular weight of 10,000 or more, 30,000 or more, or 50,000 or more. A polymer having a number average molecular weight within the range can have sufficient heat resistance, mechanical strength, and solvent resistance. The number average molecular weight may be 5,000,000 or less, 1,000,000 or less, 500,000 or less, or 100,000 or less. Typically, a polymer having a low solubility is likely to gelate and has such a disadvantage as to give a coating with a rough surface, but a polymer having a number average molecular weight within the range does not gelate and is a stable polymer.

The polymer of the present invention has a number average molecular weight of 5,000 to 5,000,000, 5,000 to 1,000,000, 5,000 to 500,000, 5,000 to 100,000, 10,000 to 5,000,000, 10,000 to 1,000,000, 10,000 to 500,000, 10,000 to 100,000, 30,000 to 5,000,000, 30,000 to 1,000,000, 30,000 to 500,000, 30,000 to 100,000, 50,000 to 5,000,000, 50,000 to 1,000,000, 50,000 to 500,000, or 50,000 to 100,000, for example.

The polymer of the present invention may have a weight average molecular weight of 5,000 or more, 10,000 or more, or 50,000 or more. A polymer having a weight average molecular weight within the range can have sufficient heat resistance, mechanical strength, and solvent resistance. The weight average molecular weight may be 2,000,000 or less, 1,000,000 or less, or 500,000 or less. A polymer having a weight average molecular weight within the range does not gelate and is a stable polymer.

The polymer of the present invention has a weight average molecular weight of 5,000 to 2,000,000, 5,000 to 1,000,000, 5,000 to 500,000, 10,000 to 2,000,000, 10,000 to 1,000,000, 10,000 to 500,000, 50,000 to 2,000,000, 50,000 to 1,000,000, or 50,000 to 500,000, for example.

The number average molecular weight and the weight average molecular weight are determined by gel permeation chromatography (GPC) relative to polystyrene standards.

When comprising at least 1% by mole of the structural unit represented by Formula (2), the polymer of the present invention can have such biocompatibility as to be practically used. When comprising the structural unit represented by Formula (2) at a higher content, the polymer has higher biocompatibility. The content of the structural unit represented by Formula (2) is preferably 5% by mole or more, more preferably 10% by mole or more, and even more preferably 30% by mole or more. A polymer having a content within the range can be used in a wide variety of medical fields. The upper limit of the content of the structural unit represented by Formula (2) is typically about 70% by mole.

In the polymer of the present invention, the content of the structural unit represented by Formula (2) is 5 to 70% by mole, 10 to 70% by mole, or 30 to 70% by mole, for example.

The content of the structural unit represented by Formula (2) can be adjusted to an intended value by controlling the proportion of the compound represented by Formula (1) in the material compounds (including monomers and/or prepolymers) to be polymerized.

The polymer of the present invention exerts sufficient biocompatibility even when comprising the structural unit represented by Formula (2) at a low content. Hence, the polymer can be produced inexpensively by using an inexpensive monomer or prepolymer at a higher proportion.

Method for Producing Polymer of Present Invention

The polymer having the structural unit represented by Formula (2) can be produced by polymerizing the compound represented by Formula (1) with an additional polymerizable monomer or with a prepolymer having a reactive functional group.

The additional polymerizable monomer can have a functional group that can undergo, together with a functional group contained in the substituent A of the compound of Formula (1), polycondensation reaction, polyaddition reaction, or radical polymerization reaction to give a bond. The number of the functional groups in the additional polymerizable monomer can be two or more when the substituent A of Formula (1) comprises an amino group, a hydroxy group, or an epoxy group, or can be one or more when the substituent A of Formula (1) comprises a (meth)acryloyl group.

In addition to such an additional polymerizable monomer, a monomer that has a phosphorylcholine group or a sulfobetaine group and is other than the compound of Formula (1) can be used as long as the effect of the invention is not impaired.

The prepolymer having a reactive functional group may have, at a terminal, a reactive functional group that can undergo, together with the functional group A of the compound of Formula (1), polycondensation reaction, polyaddition reaction, or radical polymerization reaction to give a bond. The terminal may be either a main chain terminal or a side chain terminal. The number of the reactive functional groups in the prepolymer can be two or more when the substituent A of Formula (1) comprises an amino group, a hydroxy group, or an epoxy group, or can be one or more when the substituent A of Formula (1) comprises a (meth)acryloyl group.

When the compound of Formula (1) is reacted with the prepolymer, a monomer that has a phosphorylcholine group or a sulfobetaine group and is other than the compound of Formula (1) can also be used as long as the effect of the invention is not impaired.

(For Polymerization with Additional Polymerizable Monomer)

(a) When a is a Substituent Comprising an Amino Group

When A is a substituent comprising an amino group in the compound of Formula (1), the additional polymerizable monomer can be a dicarboxylic acid or a derivative thereof, a tetracarboxylic dianhydride, a diisocyanate, or the like.

The additional polymerizable monomers may be used singly or in combination of two or more of them.

When a dicarboxylic acid or a derivative thereof is used as the additional polymerizable monomer, a polyamide having an amide bond in the main chain skeleton can be produced.

The dicarboxylic acid or a derivative thereof used as the additional polymerizable monomer can be, for example, a compound represented by Formula (16):

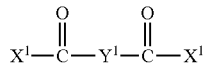

(16)

(where $Y^1$ is a divalent organic group, preferably a divalent organic group derived from a dicarboxylic acid; and $X^1$ is a hydroxy group, a halogen atom, or an alkoxy group).

In this case, a resulting polyamide has a repeating unit represented by Formula (17):

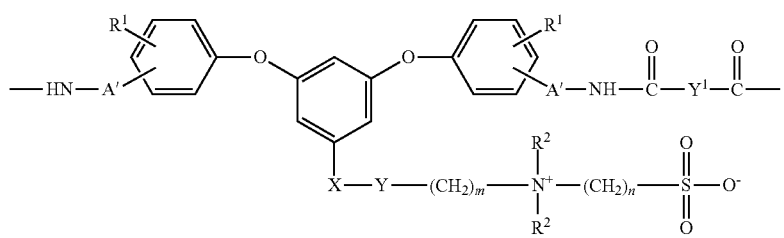

(17)

(where $Y^1$ is a divalent organic group, preferably a divalent organic group derived from a dicarboxylic acid; A' is a residue obtained by removing an amino group from A in Formula (1); and $R^1$, $R^2$, $R^3$, X, Y, m, and n are as defined in Formula (2)).

Specific examples of the dicarboxylic acid or a derivative thereof represented by Formula (16) include aromatic dicarboxylic acids such as phthalic acid, terephthalic acid, isophthalic acid, 2,6-naphthalenedicarboxylic acid, 1,6-naphthalenedicarboxylic acid, 2,6-anthracenedicarboxylic acid, 1,6-anthracenedicarboxylic acid, 4,4'-biphenyldicarboxylic acid, 4,4'-diphenylmethanedicarboxylic acid, 4,4'-diphenyl ether dicarboxylic acid, 2,2-bis(4-carboxyphenyl)propane, and 2,2-bis[4-(4-carboxyphenylphenoxy)phenyl]propane; heterocyclic dicarboxylic acids such as 2,5-furandicarboxylic acid; saturated aliphatic dicarboxylic acids such as oxalic acid, malonic acid, succinic acid, glutaric acid, adipic acid, pimelic acid, suberic acid, azelaic acid, sebacic acid, and tartaric acid; unsaturated aliphatic dicarboxylic acids such as fumaric acid, maleic acid, and itaconic acid; cycloalkane dicarboxylic acids such as 1,9-nonanedicarboxylic acid and 1,10-decanedicarboxylic acid; cycloalkene dicarboxylic acids such as cis-4-cyclohexene-1,2-dicarboxylic acid; dicarboxylic amino acids such as aspartic acid and glutamic acid; and acid anhydrides, acid halides, and alkyl esters thereof.

Of them, an aromatic dicarboxylic acid is preferred, and 2,2-bis[4-(4-chlorocarbonylphenyloxy)phenyl]propane is more preferred.

The dicarboxylic acids and derivatives thereof may be used singly or in combination of two or more of them.

When a tetracarboxylic dianhydride is used as the additional polymerizable monomer to give a polyamic acid, and the polyamic acid is subjected to imidization by heat treatment or by dehydration and cyclization with a catalyst such as an amine catalyst, a polyimide having an imide bond in the main chain skeleton can be produced.

The tetracarboxylic dianhydride used as the additional polymerizable monomer can be, for example, a compound represented by Formula (18):

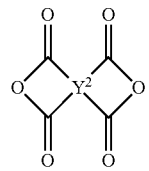

(18)

(where $Y^2$ is a tetravalent organic group, preferably a tetravalent organic group derived from a tetracarboxylic acid).

In this case, a polyamic acid can be once prepared, and the polyamic acid can be imidized to give a polyimide. The resulting polyimide has a repeating unit represented by Formula (19):

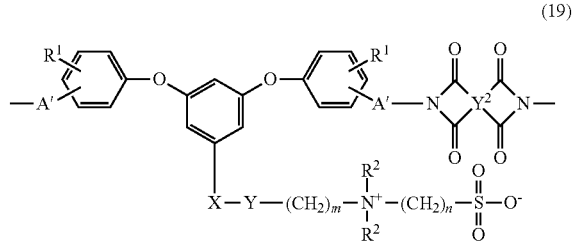

(19)

(where $Y^2$ is a tetravalent organic group, preferably a tetravalent organic group derived from a tetracarboxylic acid; A' is a residue obtained by removing an amino group from A in Formula (1); and $R^1$, $R^2$, $R^3$, X, Y, m, and n are as defined in Formula (2)).

Specific examples of the tetracarboxylic dianhydride represented by Formula (18) include pyromellitic dianhydride, 2,3,6,7-naphthalenetetracarboxylic dianhydride, 1,2,5,6-naphthalenetetracarboxylic dianhydride, 1,4,5,8-naphthalenetetracarboxylic dianhydride, 2,3,6,7-anthracenetetracarboxylic dianhydride, 1,2,5,6-anthracenetetracarboxylic dianhydride, 3,3',4,4'-diphenyltetracarboxylic dianhydride, bis(3,4-dicarboxyphenyl) ether dianhydride, 3,3',4,4'-benzophenonetetracarboxylic dianhydride, bis(3,4-dicarboxyphenyl)sulfone dianhydride, bis(3,4-dicarboxyphenyl)methane dianhydride, 2,2-bis(3,4-dicarboxyphenyl)propane dianhydride, 1,1,1,3,3,3-hexafluoro-2,2-bis(3,4-dicarboxyphenyl)propane dianhydride, bis(3,4-dicarboxyphenyl)dimethylsilane dianhydride, bis(3,4-dicarboxyphenyl)diphenylsilane dianhydride, 2,3,5,6-pyridinetetracarboxylic dianhydride, 2,6-bis(3,4-dicarboxyphenoxy)pyridine dianhydride, cyclobutanetetracarboxylic dianhydride, cyclopentanetetracarboxylic dianhydride, cyclohexanetetracarboxylic dianhydride, and 3,4-dicarboxy-1,2,3,4-tetrahydro-1-naphthalene-succinic acid dianhydride.

The tetracarboxylic dianhydrides may be used singly or in combination of two or more of them.

When a diisocyanate compound is used as the additional polymerizable monomer, a polyurea having a urea bond in the main chain skeleton can be produced.

The diisocyanate compound used as the additional polymerizable monomer can be, for example, a compound represented by Formula (20):

(where $Y^3$ is a divalent organic group, preferably a divalent organic group derived from a diisocyanate compound).

In this case, the resulting polyurea has a repeating unit represented by Formula (21):

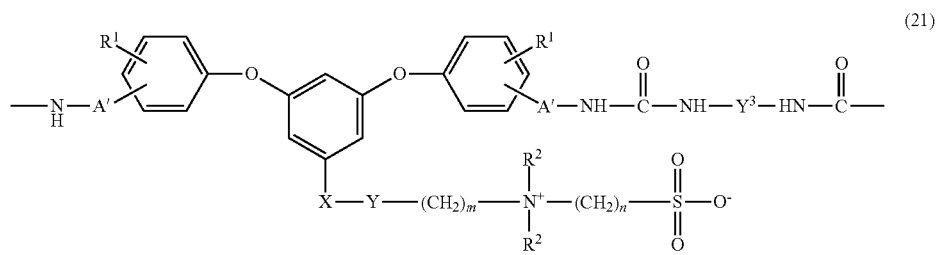

(where $Y^3$ is a divalent organic group, preferably a divalent organic group derived from a diisocyanate compound; A' is a residue obtained by removing an amino group from A in Formula (1); and $R^1$, $R^2$, $R^3$, X, Y, m, and n are as defined in Formula (2)).

Specific examples of the diisocyanate compound represented by Formula (20) include 1,4-phenylene diisocyanate, 1,3-phenylene diisocyanate, 1,4-xylylene diisocyanate, 1,3-xylylene diisocyanate, 2,4-toluylene diisocyanate, 2,5-toluylene diisocyanate, 4,4'-biphenylene diisocyanate, 4,4'-diphenyl ether diisocyanate, 4,4'-diphenylmethane diisocyanate, 4,4'-(2,2-diphenylpropane) diisocyanate, tetramethylene diisocyanate, pentamethylene diisocyanate, hexamethylene diisocyanate, heptamethylene diisocyanate, and octamethylene diisocyanate.

Of them, 4,4'-diphenylmethane diisocyanate or hexamethylene diisocyanate is preferred, and 4,4'-diphenylmethane diisocyanate is more preferred.

The diisocyanate compounds may be used singly or in combination of two or more of them.

(b) When a is a Substituent Comprising a Hydroxy Group

When A is a substituent comprising a hydroxy group in the compound of Formula (1), the additional polymerizable monomer can be a diisocyanate compound, a dicarboxylic acid, a derivative thereof, or the like.

When a diisocyanate compound is used as the additional polymerizable monomer, a polyurethane having a urethane bond in the main chain skeleton can be produced. The structural formula, specific examples, and preferred examples of the diisocyanate compound are the same as the case in which the functional group A is a substituent comprising an amino group.

The resulting polyurethane has a repeating unit represented by Formula (22):

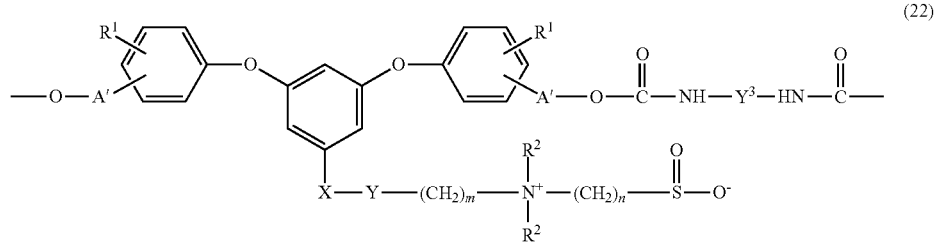

(where $Y^3$ is a divalent organic group, preferably a divalent organic group derived from a diisocyanate compound; A' is a residue obtained by removing a hydroxy group from A in Formula (1); and $R^1$, $R^2$, $R^3$, X, Y, m, and n are as defined in Formula (2)).

The diisocyanate compounds may be used singly or in combination of two or more of them.

When a dicarboxylic acid or a derivative thereof is used as the additional polymerizable monomer, a polyester having an ester bond in the main chain skeleton can be produced. The structural formula, specific examples, and preferred examples of the dicarboxylic acid or a derivative thereof are the same as the case in which the functional group A is a substituent comprising an amino group.

The resulting polyurethane has a repeating unit represented by Formula (23):

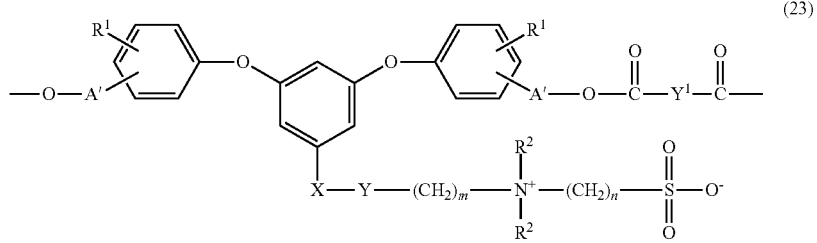

(where $Y^1$ is a divalent organic group, preferably a divalent organic group derived from a dicarboxylic acid; A' is a residue obtained by removing a hydroxy group from A in Formula (1); and $R^1$, $R^2$, $R^3$, X, Y, m, and n are as defined in Formula (2)).

The dicarboxylic acids and derivatives thereof may be used singly or in combination of two or more of them.

(c) When a is a Substituent Comprising an Epoxy Group

When A is a substituent comprising an epoxy group in the compound of Formula (1), the additional polymerizable monomer can be an epoxy compound other than the compound of Formula (1), a dicarboxylic acid or a derivative thereof, a polyol compound, a diisocyanate compound, or the like.

When a dicarboxylic acid or a derivative thereof is used as the additional polymerizable monomer, a polyester-type epoxy polymer can be produced. When a polyol compound is used as the additional polymerizable monomer, a polyether-type epoxy polymer can be produced. When a diisocyanate compound is used as the additional polymerizable monomer, a polyurethane-type epoxy polymer can be produced.

Specific examples of the epoxy compound other than the compound of Formula (1) include diglycidyl ethers having a heterocycle and having a fused ring structure or a spiro ring structure in the molecule, such as isosorbide diglycidyl ether, isomannide diglycidyl ether, isoidide diglycidyl ether, spiroglycol diglycidyl ether, and 2,4:3,5-di-O-methylene-mannitol diglycidyl ether; diglycidyl ethers having a heterocycle, such as 1,4-dioxane-2,5-diglycidyl ether and 2,3:4,5-di-O-methylene-galactose diglycidyl ether; and glycidyl ether of ethylene glycol, glycol or polyethylene glycol.

The epoxy compounds other than the compound of Formula (1) may be used singly or in combination of two or more of them.

Specific examples of the dicarboxylic acid or a derivative thereof are the same as the case in which the substituent A is a substituent comprising an amino group. The dicarboxylic acids and derivatives thereof may be used singly or in combination of two or more of them.

Specific examples of the polyol compound include bisphenols except endocrine disruptors, such as bisphenol F, bisphenol C, bisphenol K, bisphenol Z, bisphenol S, tetramethylbisphenol A, tetramethylbisphenol F, tetramethylbisphenol S, tetramethylbisphenol Z, dihydroxydiphenyl sulfide, and 4,4'-thiobis(3-methyl-6-tert-butylphenol); dihydroxybenzenes such as catechol, resorcin, methylresorcin, hydroquinone, monomethylhydroquinone, dimethylhydroquinone, trimethylhydroquinone, mono-tert-butylhydroquinone, and di-tert-butylhydroquinone; dihydroxynaphthalenes such as dihydroxynaphthalene, dihydroxymethylnaphthalene, and dihydroxydimethylnaphthalene; dihydroxyanthracenes such as dihydroxyanthracene, dihydroxymethylanthracene, and dihydroxydimethylanthracene; dihydroxyfluorenes such as 9,9'-bis(4-hydroxyphenyl)fluorene and 9,9'-bis(4-hydroxy-3-methylphenyl)fluorene; alicyclic polyols such as 1,4-cyclohexanedimethanol; polyols having a heterocycle, such as isosorbide, isomannide, isoidide, spiroglycol, 2,4:3,5-di-O-methylene-mannitol, and 2,3:4,5-di-O-methylene-galactose; and aliphatic polyols such as sorbitol, mannitol, galactose, ethylene glycol, and glycol.

The polyol compounds may be used singly or in combination of two or more of them.

Specific examples of the diisocyanate compound are the same as the case in which the substituent A is a substituent comprising an amino group. The diisocyanate compounds may be used singly or in combination of two or more of them.

(d) When a is a Substituent Comprising a (Meth)Acryloyl Group

When A is a substituent comprising a (meth)acryloyl group in the compound of Formula (1), the additional polymerizable monomer can be a (meth)acrylic compound ((meth)acrylic acid or a (meth)acrylate) or the like.

The (meth)acrylic compound used can be, for example, a compound represented by Formula (24):

$$H_2C=C\begin{matrix}R^4\\R^5\end{matrix} \quad (24)$$

(where $R^4$ is a hydrogen atom or a methyl group; and $R^5$ is an organic group).

In this case, the resulting polymer has a repeating unit represented by Formula (25):

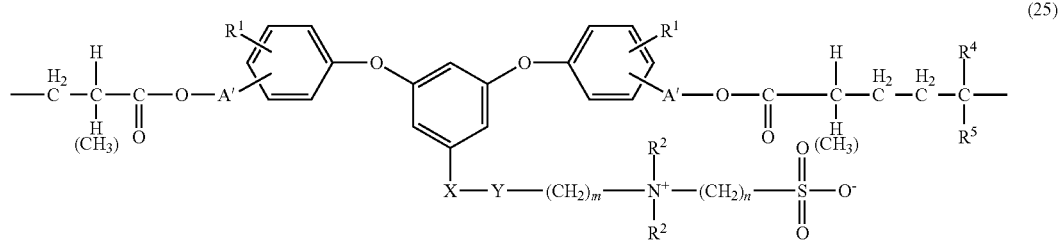

(25)

(where $R^4$ is a hydrogen atom or a methyl group; $R^5$ is an organic group; A' is a residue obtained by removing a (meth)acryloyl group from A in Formula (1); and $R^1$, $R^2$, $R^3$, X, Y, m, and n are as defined in Formula (2)).

Specific examples of the (meth)acrylic compound represented by Formula (24) include monofunctional monomers such as methyl (meth)acrylate, ethyl (meth)acrylate, n-butyl (meth)acrylate, isobutyl (meth)acrylate, t-butyl (meth)acrylate, neopentyl (meth)acrylate, cyclohexyl (meth)acrylate, benzyl (meth)acrylate, octyl (meth)acrylate, lauryl (meth)acrylate, stearyl (meth)acrylate, cetyl (meth)acrylate, ethyl carbitol (meth)acrylate, hydroxyethyl (meth)acrylate, hydroxypropyl (meth)acrylate, hydroxybutyl (meth)acrylate, methoxyethyl (meth)acrylate, methoxybutyl (meth)acrylate, N-methyl(meth)acrylamide, N-ethyl(meth)acrylamide, n-propyl(meth)acrylamide, N-isopropyl(meth)acrylamide, N-butoxymethyl(meth)acrylamide, N-t-butyl(meth)acrylamide, N-octyl(meth)acrylamide, N,N-dimethyl(meth)acrylamide, N,N-diethyl(meth)acrylamide, (meth)acryloyl morpholine, diacetone(meth)acrylamide, styrene, methyl itaconate, ethyl itaconate, vinyl acetate, vinyl propionate, N-vinylpyrrolidone, and N-vinylcaprolactam; and polyfunctional monomers such as 1,4-butanediol di(meth)acrylate, 1,6-hexanediol di(meth)acrylate, 1,9-nonanediol di(meth)acrylate, 2-n-butyl-2-ethyl-1,3-propanediol di(meth)acrylate, tripropylene glycol di(meth)acrylate, tetraethylene glycol di(meth)acrylate, methylenebisacrylamide, trimethylolpropane tri(meth)acrylate, and pentaerythritol tri(meth)acrylate.

The (meth)acrylic compounds may be used singly or in combination of two or more of them.

(For Polymerization with Prepolymer Having Reactive Functional Group at Terminal)

Examples of the prepolymer having a reactive functional group at a terminal include an isocyanate group-terminated urethane prepolymer prepared by reacting an excess amount of a diisocyanate compound with a diol compound by a known method.

By reacting an isocyanate group-terminated urethane prepolymer with a compound of Formula (1) in which the functional group A is a substituent comprising an amino group, a urea bond can be formed to yield a poly(urethane-urea) having a urethane bond and a urea bond in the main chain skeleton.

By reacting an isocyanate group-terminated urethane prepolymer with a compound of Formula (1) in which the functional group A is a substituent comprising a hydroxy group, a urethane bond can be formed to yield a polyurethane.

Examples of the usable diol compound include hydroquinone, 1,3-phenylenediol, 1,4-xylylenediol, 1,3-xylylenediol, 2,4-toluylene diol, 2,5-toluylene diol, 4,4'-biphenylene diol, 4,4'-diphenyl ether diol, 4,4'-diphenylmethane diol, ethylene glycol, propylene glycol, tetramethylene glycol, pentamethylene glycol, hexamethylene glycol, heptamethylene glycol, octamethylene glycol, polyethylene glycol, polypropylene glycol, polytetraethylene oxide, □,□-bis(hydroxypropyl)polydimethylsiloxane, □,□-bis(hydroxyethoxypropyl)polydimethylsiloxane, polytetramethylene ether glycol, and polycarbonate diol.

Of them, polycarbonate diol or polytetramethylene ether glycol is preferred, and polycarbonate diol is more preferred.

The diol compounds may be used singly or in combination of two or more of them.

Examples of the diisocyanate compound usable for the synthesis of the isocyanate group-terminated urethane prepolymer include those exemplified as the polymerizable monomers to be copolymerized with the compound of Formula (1).

Of them, 4,4'-diphenylmethane diisocyanate or hexamethylene diisocyanate is preferred, and 4,4'-diphenylmethane diisocyanate is more preferred.

The diisocyanate compounds may be used singly or in combination of two or more of them.

The diol compound used for the synthesis of the urethane prepolymer serves as a soft segment in the polymer of the present invention produced after the polymerization with the compound of Formula (1). Hence, the diol compound preferably has a number average molecular weight of 800 or more and more preferably 1,000 or more. Within the range, the polymer of the present invention obtains sufficient flexibility. The diol compound preferably has a number average molecular weight of 3,000 or less and more preferably 2,000 or less. Within the range, the polymer of the present invention obtains sufficient mechanical strength. The diol compound used for the synthesis of the urethane prepolymer has a number average molecular weight of 800 to 3,000, 800 to 2,000, 1,000 to 3,000, or 1,000 to 2,000, for example.

The molar ratio of the diol compound used for the synthesis of the urethane prepolymer and the compound of Formula (1) (diol compound:compound of Formula (1)) can be about 4:6 to 8:2 and is specifically preferably about 5:5 to 7:3.

(Coexisting Polymerizable Monomer)

The compound represented by Formula (1) is a rigid compound and thus is likely to give a rigid polymer depending on the type of the additional polymerizable monomer or the prepolymer having a reactive functional group. Some medical materials are desirably flexible to some extent in order not to apply mechanical stress to a living organism. For such a purpose, in the polymerization the compound represented by Formula (1), a polymerizable monomer having two or more of the same functional groups as the functional group contained in the substituent A of the compound of Formula (1) is desirably allowed to coexist to control the flexibility of the polymer.

The proportion of the compound of Formula (1) used in this case is preferably 1% by mole or more and more preferably 5% by mole or more relative to the total amount of the compound of Formula (1) and the coexisting polymerizable monomer. Within the range, sufficient heat resistance and mechanical strength are achieved. The upper limit of the proportion may be about 50% by mole. Within the range, a resulting polymer obtains appropriate flexibility. The proportion of the compound of Formula (1) is, for example, 1 to 50% by mole or 5 to 50% by mole relative to the total amount the compound of Formula (1) and the coexisting polymerizable monomer.

As the polymerizable monomer having two or more of the same functional groups as the functional group contained in the substituent A of the compound of Formula (1), a diamine compound or the like can be used when the functional group contained in A of the compound of Formula (1) is an amino group, a diol compound or the like can be used when the functional group contained in A of the compound of Formula (1) is a hydroxy group, a diepoxy compound or the like can be used when the functional group contained in A of the compound of Formula (1) is an epoxy group, and a (meth) acrylic compound having (meth)acryloyl groups at both terminals (either main chain terminals or side chain terminals) can be used when the functional group contained in A of the compound of Formula (1) is a (meth)acryloyl group. These coexisting polymerizable monomers may be used singly or in combination of two or more of them.

In order to improve the flexibility of the polymer of the present invention, the coexisting polymerizable monomer preferably has a glass transition point of 0° C. or less.

Examples of the diamine compound coexisting with the compound represented by Formula (1) include 1,4-phenylenediamine, 1,3-phenylenediamine, 2,5-diaminotoluene, 2,6-diaminotoluene, 4,4'-diaminobiphenyl, 3,3'-dimethyl-4,4'-diaminobiphenyl, 3,3'-dimethoxy-4,4'-diaminobiphenyl, 4,4'-diaminodiphenylmethane, 4,4'-diamino-3,3'-dimethyldiphenylmethane, 4,4'-diaminodiphenyl ether, 2,2-bis(4-aminophenyl)propane, 4,4'-diaminodiphenylsulfone, 4,4'-diaminobenzophenone, 1,4-bis(4-aminophenyl)benzene, 1,4-bis(4-aminophenyloxy)benzene, 4,4'-bis(4-aminophenyloxy)diphenylsulfone, 2,2-bis[4-(4-aminophenyloxy)phenyl]propane, bis(4-aminocyclohexyl)methane, piperazine, 2-methylpiperazine, ethylenediamine, 1,3-diaminopropane, tetramethylenediamine, pentamethylenediamine, hexamethylenediamine, heptamethylenediamine, octamethylenediamine, nonamethylenediamine, decamethylenediamine, and dodecamethylenediamine.

(Applications of Polymer of Present Invention)

The polymer of the present invention can be used as materials of medical products to be implanted in a living organism, including an artificial blood vessel, a prosthetic cardiac valve, an artificial joint, an artificial skin, an artificial tissue, a cell growth scaffold for an artificial bone, a dental material, a tissue adhesion material, a cardiac pacemaker, a stent, and a surgical suture, materials of medical products to be in contact with a living organism, including a catheter, a contact lens, a base material for sustained release drugs, and an endoscope, materials of medical products to be in contact with a material separated from a living organism, including a hemodialysis membrane and a blood storage bag, and covering materials for such medical products.

The polymer of the present invention may be used singly or may be used as a mixture with other polymers as long as the effect of the invention is not impaired.

The polymer of the present invention has both high rupture strength and high breaking elongation and thus is preferably molded into a film, a sheet, fibers, or a membrane, for example.

EXAMPLES

The present invention will next be described in further detail with reference to examples, but the present invention is not limited thereto.

(1) Synthesis of Sulfobetaine Group-Containing Diamine

A sulfobetaine group-containing diamine was synthesized in accordance with the following scheme.

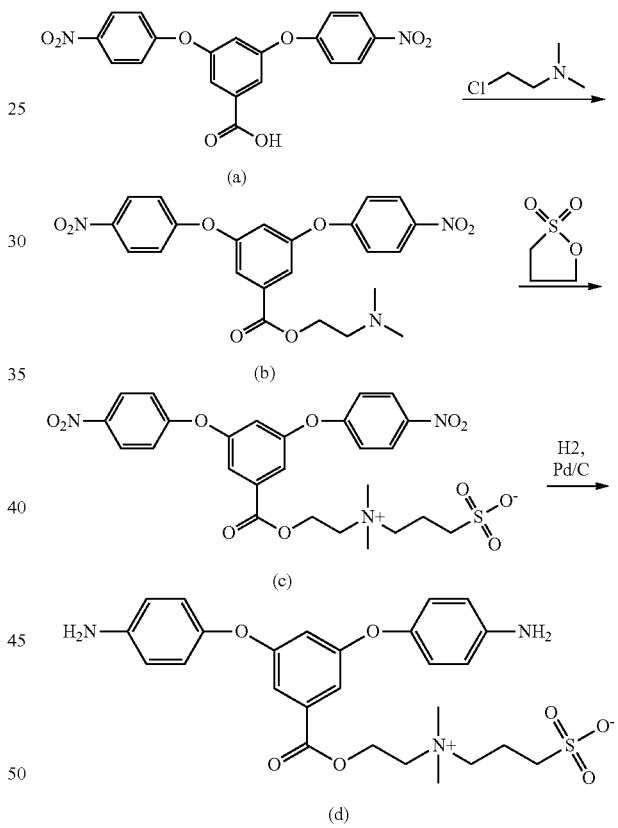

Synthesis of Compound (a)

In a recovery flask, methyl 3,5-dihydroxybenzoate (30.0 g, 148.5 mmol) was dissolved in dimethylacetamide (300 ml) by stirring, then to the obtained solution, 4-fluoronitrobenzene (50.3 g, 357 mmol) and potassium carbonate (49.3 g, 357 mmol) were added, and the whole was reacted at 85° C. for 16 hours. After the completion of the reaction, the reaction mixture was poured into distilled water, and the resulting precipitate was suction filtered. The solid was vacuum dried at 40° C. to give 61.1 g of a compound that is a methyl ester of the calboxylic compound (a), as a white solid (yield 100%).

In a recovery flask, the compound obtained by the above reaction (72.8 g, 177.7 mmol), acetic acid (525 ml), sulfuric acid (525 ml), and distilled water (140 ml) were stirred and mixed, and the mixture was refluxed at 120° C. for 18 hours. After the completion of the reaction, the reaction mixture was poured into distilled water, and the resulting precipitate was suction filtered. The solid was vacuum dried at 40° C. to give 66.3 g of a compound (a) as a white solid (yield 94%).

Synthesis of Compound (b)

In a recovery flask, the compound (a) (41 g, 103.5 mmol), 2-(dimethylamino) ethyl chloride hydrochloride (17.9 g, 124.2 mmol), and potassium carbonate (28.6 g, 207 mmol) were dissolved in dimethylacetamide (400 ml) by stirring, and the whole was reacted at 110° C. for 24 hours. After the completion of the reaction, dimethylacetamide was distilled off under reduced pressure, then the residue was extracted with chloroform, and the extract was washed with 0.5N hydrochloric acid and an aqueous sodium hydrogen carbonate solution. The organic phase was dehydrated with sodium sulfate and filtered, and then the solvent was distilled off under reduced pressure, giving 46 g of a compound (b) as a yellow solid (yield 95%).

The structure of the compound was ascertained from the following LC-MS spectrum.

LC-MS(ES): Calcd. for $C_{23}H_{22}N_3O_8$ 468.1 $[M+H]+$, Found: 468.3

Synthesis of Compound (c)

In a recovery flask, the compound (b) (6.0 g, 12.8 mmol) was dissolved in chloroform (75 ml) by stirring, then 1,3-propane sultone (9.4 g, 76.8 mmol) was added, and the whole was reacted at 45° C. for 13 hours. After the completion of the reaction, the precipitated white solid was suction filtered. The solid was vacuum dried at 40° C. to give 7.2 g of a compound (c) as a white solid (yield 95%).

The structure of the compound was ascertained from the following LC-MS spectrum.

LC-MS(ES): Calcd. for $C_{26}H_{28}N_3O_{11}S$ 590.1 $[M+H]+$, Found: 590.5

Synthesis of Sulfobetaine Group-Containing Diamine (d)

In a recovery flask, the compound (c) (300 mg, 0.51 mmol) was dispersed in methanol (15 ml), and 5% palladium-carbon powder (30 mg) was added thereto. The system was purged with hydrogen, and the reaction was performed at 25° C. for 16 hours. After the completion of the reaction, methanol was removed under reduced pressure to about ⅒ in terms of volume, then the concentrate was poured into diethyl ether, and the precipitate was suction filtered. The solid was vacuum dried at 40° C. to give 240 mg of a sulfobetaine group-containing diamine (d) as a brown solid (yield 89%).

The structure of the compound was ascertained from the following LC-MS spectrum.

LC-MS(ES): Calcd. for $C_{26}H_{32}N_3O_7S$ 530.2 $[M+H]+$, Found: 530.6

(2) Synthesis of Segmented Polyurethaneurea Containing Sulfobetaine Group (SPUUSB)

Example 1

In a nitrogen atmosphere, polycarbonate diol (a number average molecular weight of 1,000) (3.3 g, 3.3 mmol) and dimethylsulfoxide (1 ml) were placed in a three-necked flask, then were heated to 70° C., and were dissolved. To the solution, a solution of 4,4'-diphenylmethane diisocyanate (1.6 g, 6.6 mmol) in dimethylsulfoxide (2 ml) was added dropwise at room temperature. After the completion of the dropwise addition, the mixture was reacted at 70° C. for 1 hour. After the completion of the reaction, a solution of the sulfobetaine group-containing diamine (d) (1.7 g, 3.3 mmol) in dimethylsulfoxide (10 ml) was added dropwise at room temperature. After the completion of the dropwise addition, the mixture was reacted at 70° C. for 24 hours. After the completion of the reaction, the reaction solution was poured into an excess amount of methanol, and the resulting precipitate was suction filtered. The obtained solid was vacuum dried at 40° C. to give 6.2 g of a segmented polyurethaneurea containing a sulfobetaine group (SPUUSB) as a brown solid (yield 91.8%).

Example 2

The same procedure as in Example 1 was performed except that the polycarbonate diol in Example 1 was used in an amount of 4.66 g (4.66 mmol), and the sulfobetaine group-containing diamine (d) was used in an amount of 1.06 g (2.0 mmol), giving 6.5 g of a segmented polyurethaneurea containing a sulfobetaine group (SPUUSB30) as a brown solid (yield 88.8%).

Example 3

The same procedure as in Example 1 was performed except that a sulfobetaine group-containing diamine synthesized by using butane sultone in place of propane sultone to be reacted with the compound (b) was used at the same monomer ratio as in Example 1, giving 2.48 g of a segmented polyurethaneurea containing a sulfobetaine group (SPUUSBB) as a brown solid (yield 86.1%).

Example 4

The same procedure as in Example 3 was performed except that the polycarbonate diol in Example 3 was used in an amount of 3.7 g (3.7 mmol), and the sulfobetaine group-containing diamine (d) was used in an amount of 0.87 g (1.6 mmol), giving 5.32 g of a segmented polyurethaneurea containing a sulfobetaine group (SPUUSBB30) as a brown solid (yield 89.3%).

Example 5

The same procedure as in Example 3 was performed except that in place of the polycarbonate diol having a number average molecular weight of 1,000 in Example 3, a polycarbonate diol having a number average molecular weight of 2,000 was used at the same molar ratio as in Example 3, giving 8.6 g of a segmented polyurethaneurea containing a sulfobetaine group (SPUUSBBR) as a brown solid (yield 84.8%).

Example 6

The same procedure as in Example 3 was performed except that a sulfobetaine group-containing diamine synthesized by using 2-(dimethylamino)hexyl chloride hydrochloride in place of 2-(dimethylamino)ethyl chloride hydrochloride to be reacted with the compound (a) was used at the same monomer ratio as in Example 3, giving 2.74 g of a segmented polyurethaneurea containing a sulfobetaine group (SPUUSBB6) as a brown solid (yield 51.6%).

(3) Synthesis of Segmented Polyurethaneurea Having No Sulfobetaine Group (SPUU)

Comparative Example 1

In a nitrogen atmosphere, polycarbonate diol (1.1 g, 1.11 mmol) and dimethylsulfoxide (1 ml) were placed in a three-necked flask, then were heated to 70° C., and were dissolved. To the solution, a solution of 4,4'-diphenylmethane diisocyanate (0.5 g, 2.2 mmol) in dimethylsulfoxide (2 ml) was added dropwise at room temperature. After the completion of the dropwise addition, the mixture was reacted at 70° C. for 1 hour. After the completion of the reaction, a solution of 1,3-bis (4-aminophenoxy)benzene (0.33 g, 1.1 mmol) in dimethylsulfoxide (10 ml) was added dropwise at room temperature. After the completion of the dropwise addition, the mixture was reacted at 70° C. for 24 hours. After the completion of the reaction, the reaction solution was poured into an excess amount of methanol, and the resulting precipitate was suction filtered. The obtained solid was vacuum dried at 40° C. to give 1.69 g of a segmented polyurethaneurea (SPUU) as a brown solid (yield 87.3%).

(4) Molecular Weight Determination of Polymer

The weight average molecular weight and the number average molecular weight of each segmented polyurethaneurea resin obtained in Examples 1 to 6 and Comparative Example 1 were determined by gel permeation chromatography in terms of standard polystyrene in the following conditions.

(GPC Conditions)
Apparatus: Shodex GPC-104 system (manufactured by SHOWA DENKO K.K.)
Column: Shodex GPC KD-806M (manufactured by SHOWA DENKO K.K.)
Guard column: KF-G (manufactured by SHOWA DENKO K.K.)
Sample concentration: 1% by weight, diluted with THF
Mobile phase solvent: tetrahydrofuran (THF)
Flow rate: 1.0 mL/min
Column temperature: 40° C.

(5) Thermophysical Property Evaluation of Polymer
(5% Weight Loss Temperature)

The decomposition start temperature of each segmented polyurethaneurea resin obtained in Examples 1 to 6 and Comparative Example 1 was determined in the following conditions.
Apparatus: thermogravimetric analyzer TG/DTA (manufactured by Seiko Instruments Inc.)
Measurement range: 40° C. to 550° C.
Temperature increase rate: 10° C./min
Atmosphere: nitrogen (Glass Transition Temperature)

The glass transition temperature of each segmented polyurethaneurea resin obtained in Examples 1 to 6 and Comparative Example 1 was determined in the following conditions.
Apparatus: differential scanning calorimeter DSC-6200 (manufactured by Seiko Instruments Inc.)
Measurement range: −100° C. to 200° C.
Temperature increase rate: 10° C./min (6) Strength Evaluation of Polymer Film A 10 wt % DMF solution of each segmented polyurethaneurea resin obtained in Examples 1 to 6 and Comparative Example 1 was prepared and was used to prepare a film by solvent casting.

The rupture strength and the maximum breaking elongation of the prepared film were determined by using a tensile tester in the following conditions.
Apparatus: Strograph VG20E (manufactured by Toyo Seiki Seisaku-sho, Ltd.)
Tension rate: 12 mm/min
Test piece shape: a polymer film was processed into a rectangular shape (length: 40 mm, width: 10 mm, thickness: 0.2 mm) to give a test piece.

(7) Evaluation of Biocompatibility
(Protein Adsorptivity)

The segmented polyurethaneurea resins obtained in Examples 1 to 6 and Comparative Example 1 were dissolved in N,N-dimethylformamide to give 2.0% by weight polymer solutions. Each solution was used to form a film by solvent casting, and the film was cut out into a round shape (diameter: 14 mm, thickness: 0.2 mm) to give a test piece of the corresponding polymer film.

The test piece was immersed in a phosphate buffer and was shaken at 37° C. for 24 hours. Next, the test piece was taken out, then was immersed in a 1 mg/ml bovine serum albumin (BSA) aqueous solution, and was shaken at 37° C. for 24 hours. Next, the test piece was immersed in water at 37° C. for 5 minutes, and this washing process was repeated three times. The test piece was immersed in a 1% SDS aqueous solution, then was shaken at 37° C. for 24 hours to elute the protein adsorbed onto the surface of the test piece, and the eluate was collected. The eluate was further treated with a BCA protein assay kit (manufactured by Thermo Fisher Scientific), and the absorbance was measured at 562 nm by a microplate reader.

The absorbance at 562 nm is in proportion to the amount of the bovine serum albumin adsorbed to a test piece.

(Blood Compatibility)

The segmented polyurethaneurea resins obtained in Examples 1 to 6 and Comparative Example 1 were dissolved in N,N-dimethylformamide to give 2.0% by weight polymer solutions. Each solution was used to form a film by solvent casting, and the film was cut out into a regular square (8 mm×8 mm, thickness: 0.2 mm) to give a test piece of the corresponding polymer film.

Separately, a PET film was cut out into a regular square (8 mm×8 mm, thickness: 0.2 mm) to give a test piece of Reference Example.

Each test piece was next immersed in phosphate buffered saline at room temperature for 24 hours, then the phosphate buffered saline was removed, and the test piece was immersed in human platelet-rich plasma prepared from human blood, at 37° C. for 2 hours. The polymer film surface of the test piece was then washed three times with phosphate buffered saline. Next, 25% glutaraldehyde diluted with phosphate buffered saline was added, and the whole was allowed to stand for 2 hours to fix the platelets. Under a scanning electron microscope (SEM), the surface of the prepared sample was observed.

A sample to which no or few platelets were adsorbed was evaluated as A, a sample to which a few platelets were adsorbed was evaluated as B, a sample to which many platelets were adsorbed was evaluated as C, and a sample to which so many platelets were adsorbed to aggregate was evaluated as D.

Structure features and evaluation results of each segmented polyurethaneurea resin are shown in Table 1.

| | SPUUSB Example 1 | SPUUSB30 Example 2 | SPUUSBB Example 3 | SPUUSBB30 Example 4 | SPUUSBBR Example 5 | SPUUSBB6 Example 6 | SPUU Comparative Example 1 |
|---|---|---|---|---|---|---|---|
| $R^1$ | hydrogen atom | hydrogen atom | hydrogen atom | hydrogen atom | hydrogen atom | hydrogen atom | hydrogen atom |
| $R^2$ | methyl group | methyl group | methyl group | methyl group | methyl group | methyl group | methyl group |
| X | —COO— | —COO— | —COO— | —COO— | —COO— | —COO— | hydrogen atom |
| Y | single bond | single bond | single bond | single bond | single bond | single bond | — |
| m | 2 | 2 | 2 | 2 | 2 | 6 | — |
| n | 3 | 3 | 4 | 4 | 4 | 4 | — |
| Molar ratio of diamine compound:polycarbonate diol | 50:50 | 30:70 | 50:50 | 30:70 | 50:50 | 50:50 | 50:50 |
| Number average molecular weight of polycarbonate diol | 1,000 | 1,000 | 1,000 | 1,000 | 2,000 | 1,000 | 1,000 |
| $Mw(\times 10^3)$ | 288 | 91 | 209 | 91 | 176 | 144 | 33 |
| $Mn(\times 10^3)$ | 39 | 39 | 43 | 41 | 55 | 37 | 15 |
| Mw/Mn | 7.4 | 2.3 | 4.9 | 2.2 | 3.2 | 3.89 | 2.2 |
| 5% Weight loss temperature | 299 | 301 | 301 | 303 | 303 | 300 | 299 |
| Glass transition temperature (° C.) | −10 | −10 | −10 | −10 | −25 | −10 | −10 |
| Rupture strength (MPa) | 48.4 | 32.4 | 55 | 55 | 47.2 | 46.3 | 8.5 |
| Breaking elongation (%) | 674 | 709 | 612 | 1025 | 948 | 655 | 1038 |
| Protein adsorption amount (relative value to Comparative Example 1 (100)) | 1.9 | 0.5 | 8.2 | 0.0 | 5.4 | 15 | 100 |
| Platelet adsorption amount | C | C | A | A | B | B | C |

As shown in Table 1, the segmented polyurethaneurea resin having no sulfobetaine group in Comparative Example 1 had a markedly large protein adsorption amount and was inapplicable to living organisms. The resin also had insufficient rupture strength.

In contrast, as shown in Table 1, the polymers of Examples 1 to 6 had practically sufficient heat resistance, mechanical strength, and biocompatibility. In particular, as for the mechanical strength, both the rupture strength and the breaking elongation were practically sufficient. The polymers of Examples 3 to 5 in which n is 4 in Formula (1) had particularly high mechanical strengths and a small platelet adsorption amount, which indicated excellent biocompatibility.

Scanning electron micrographs of samples prepared by subjecting the test pieces of a PET film, Comparative Example 1, Example 4, and Example 6 to the blood compatibility test are shown in FIG. 1. The platelet adsorption to each test piece of Example 4 and Example 6 was extremely smaller than that to the test piece of Comparative Example 1.

INDUSTRIAL APPLICABILITY

The polymer of the present invention has sufficient biocompatibility and also has excellent heat resistance and mechanical strength. Accordingly, the polymer can be variously used as a medical material that is implanted in a living organism or is used in contact with a living organism or with a material separated from a living organism.

The invention claimed is:
1. A compound represented by Formula (1):

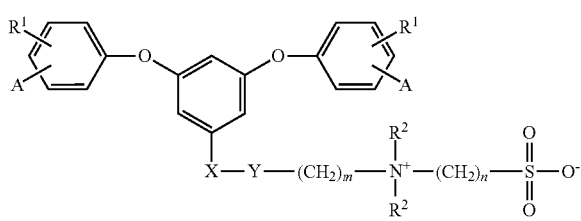

in Formula (1), two $R^1$s are the same or different from each other and are each a hydrogen atom or an alkyl group having 1 to 6 carbon atoms; substituents A are the same or different from each other and are each a substituent comprising an amino group, a hydroxy group, an epoxy group, or a (meth)acryloyl group; X is a single bond, an oxygen atom, or a group represented by —COO—, —OOC—, —CONH—, —NH—, —NHCO—, —$NR^3$—, or —$CH_2O$—; Y is a single bond or an oligooxyalkylene group; two $R^2$s are the same or different from each other and are each an alkyl group having 1 to 6 carbon atoms; $R^3$ is an alkyl group having 1 to 6 carbon atoms; m is an integer of 1 to 10; and n is an integer of 2 to 10.

2. The compound according to claim 1, wherein each substituent A is a substituent comprising an amino group.

3. The compound according to claim 1, wherein n is an integer of 3 to 5.

4. A polymer comprising at least 1% by mole of a structural unit represented by Formula (2):

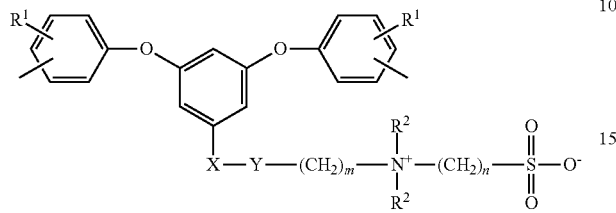

(2)

in Formula (2), two $R^1$s are the same or different from each other and are each a hydrogen atom or an alkyl group having 1 to 6 carbon atoms; X is a single bond, an oxygen atom, or a group represented by —COO—, —OOC—, —CONH—, —NH—, —NHCO—, —$NR^3$—, or —$CH_2O$—; Y is a single bond or an oligooxyalkylene group; two $R^2$s are the same or different from each other and are each an alkyl group having 1 to 6 carbon atoms; $R^3$ is an alkyl group having 1 to 6 carbon atoms; m is an integer of 1 to 10; and n is an integer of 2 to 10;

and having a number average molecular weight of 5,000 or more.

5. The polymer according to claim 4, wherein the polymer has a bond selected from the group consisting of an amide bond, a urethane bond, a urea bond, and an imide bond in a main chain skeleton thereof.

6. The polymer according to claim 4, comprising at least 1% by mole of the structural unit represented by Formula (2) and a structural unit comprising an isocyanate group-terminated urethane prepolymer prepared by reacting a diisocyanate compound and a diol compound, and having a number average molecular weight of 5,000 or more.

7. The polymer according to claim 6, wherein the polymer has a urethane bond and a urea bond in a main chain skeleton thereof.

8. The polymer according to claim 4, wherein n is an integer of 3 to 5.

9. A film, sheet, fiber, or membrane comprising the polymer according to claim 4.

10. A medical product comprising the polymer according to claim 4.

11. A method for producing the polymer according to claim 4, the method comprising:

a step of subjecting a compound represented by Formula (1):

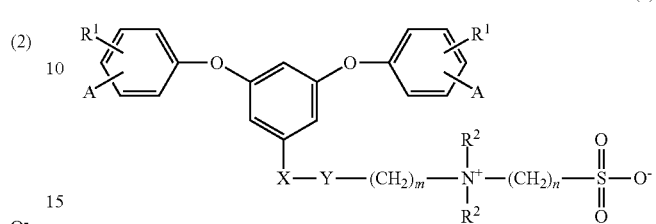

(1)

in Formula (1), two R1s are the same or different from each other and are each a hydrogen atom or an alkyl group having 1 to 6 carbon atoms; substituents A are the same or different from each other and are each a substituent comprising an amino group, a hydroxy group, an epoxy group, or a (meth)acryloyl group; X is a single bond, an oxygen atom, or a group represented by —COO—, —OOC—, —CONH—, —NH—, —NHCO—, —$NR^3$—, or —$CH_2O$—; Y is a single bond or an oligooxyalkylene group; two R2s are the same or different from each other and are each an alkyl group having 1 to 6 carbon atoms; R3 is an alkyl group having 1 to 6 carbon atoms; m is an integer of 1 to 10; and n is an integer of 2 to 10;

and an additional polymerizable monomer to polycondensation reaction, polyaddition reaction, or radical polymerization reaction or a step of reacting a polymerizable monomer comprising the compound represented by Formula (1) with a functional group-terminated prepolymer capable of reacting therewith.

12. The production method according to claim 11, wherein the produced polymer has a bond selected from the group consisting of an amide bond, a urethane bond, a urea bond, and an imide bond in a main chain skeleton thereof.

13. The production method according to claim 11, wherein the substituent A in Formula (1) comprises an amino group or a hydroxy group, and the functional group-terminated prepolymer capable of reacting with the compound represented by Formula (1) is an isocyanate group-terminated urethane prepolymer prepared by reacting a diisocyanate compound and a diol compound.

* * * * *